United States Patent [19]

Mod et al.

[11] 3,996,353
[45] Dec. 7, 1976

[54] PHOSPHONATED N,N-DISUBSTITUTED FATTY MORPHOLINES AS BACTERIAL AND FUNGICIDAL AGENTS

[75] Inventors: Robert R. Mod, New Orleans; James A. Harris, Pearl River; Jett C. Arthur, Jr.; Frank C. Magne, both of Metairie; Gene Sumrell, New Orleans; Arthur F. Novak, Baton Rouge, all of La.

[73] Assignee: The United States of America as represented by the Secretary of Agriculture, Washington, D.C.

[22] Filed: July 10, 1975

[21] Appl. No.: 594,896

Related U.S. Application Data

[62] Division of Ser. No. 335,860, Feb. 26, 1973, Pat. No. 3,911,120.

[52] U.S. Cl. .................. 424/200; 260/247.7 L; 260/268 C; 424/248
[51] Int. Cl.² ........................................... A01N 9/36
[58] Field of Search ............ 424/200; 260/247.7 L, 260/268 C

[56]  References Cited
FOREIGN PATENTS OR APPLICATIONS
1,123,863  2/1962  Germany
859,735  1/1961  United Kingdom Primary Examiner—James O. Thomas, Jr.
Assistant Examiner—Allen J. Robinson
Attorney, Agent, or Firm—M. Howard Silverstein; David G. McConnell; Salvador J. Cangemi

[57]  ABSTRACT

Phosphonated N,N-disubstituted fatty acid morpholine derivatives were prepared by the free radical addition of dialkyl phosphites to terminal and nonterminal double bonds of N,N-disubstituted fatty acid morpholine derivatives. The free radical additions of the dialkyl phosphites to the unsaturated fatty acid morpholine derivatives were initiated by irradiation with gamma radiation from cobalt-60. These new compounds exhibit antimicrobial activity.

5 Claims, No Drawings

PHOSPHONATED N,N-DISUBSTITUTED FATTY MORPHOLINES AS BACTERIAL AND FUNGICIDAL AGENTS

This is a division, of application Ser. No. 335,860, filed Feb. 26, 1973 now U.S. Pat. No. 3,911,120, issued Oct. 17, 1975.

This invention relates to new are organic compounds and to a novel for the preparation of the new compounds. More particularly, this invention relates to N,N-disubstituted long chain aliphatic amides, the acyl component of which is a normal, branched, or substituted alkenoic acyl group containing from 11 to 22 carbon atoms, the amide nitrogen of which may be derived from a dialkylamine, alkyl-alkoxyalkylamine, dialkoxyalkylamine, or nitrogen heterocyclic . . . 0020 typical amines being dibutylamines, N-methyl-N-alkoxy-ethylamine, di-ethoxyethylamine, and morpholines. The acyl substituent referred to is generally pentavalent phosphorus. )-dibutylphosphonoctadecanoyl]-carboethoxydodecancyl)morpholine.

The findings herein disclosed are considered remarkable in that in some notable instances compounds that are closely related from the point of view of chemical structure exhibit quite different effects against the same microorganisms. For example, one compound may exhibit properties as a growth inhibitor against one particular microorganism while a closely related compound may serve to promote increased growth for the same microorganism. Some of these new compounds exhibit a broad antimicrobial spectrum whereas others exhibit a selective antimicrobial spectrum. Some of the compounds produced by the process of this invention are N,N-dibutyl-9(10)-dibutylphosphonooctadecanamide, N,N-bis(2-ethoxyethyl)-9(10)-dibutylphosphonooctadecanamide, N-[9(10)-dibutylphosphonooctadecanoyl]-2,6-dimethylmorpholine, N-ethyl-N-(3-ethoxypropyl)-9(10)-dibutylphosphonooctadecanamide, N-[9,(10)-dibutylphosphonooctadecanoyl]piperidine, N-[9(10)-dibutylphosphonooctadecanoyl]-N'-methylpiperazine, N,N-dimethyl-9(10)-dibutylphosphonooctadecanamide, N[9(10)-dibutylphosphonooctadecanoyl]-4-methylpiperidine, N-methyl-N-butyl-9(10)-dibutylphosphonooctadecanamide, N-[9(10)-dibutylphosphonooctadecanoyl]morpholine, N-[11-dibutylphosphonoundecanoyl]-morpholine, and N-(12-acetyl-12-carboethoxydodecancyl)morpholine The new phosphorus-containing compounds of this invention were prepared by a novel procedure involving the free-radical addition of dialkyl phosphites to terminal and nonterminal double bonds of N,N-disubstituted amides. The free-radical additions were initiated by irradiation with gamma radiation from cobalt-60. The reaction to the internal double bond is unexpected since after attempts to initiate the reaction of dialkyl phosphites with alkyl oleates by ultra-violet irradiation, both reactants were recovered unchanged. (See "Phosphorus Derivatives of Fatty Acids. VII. Addition of Dialkyl Phosphonates to Unsaturated Compounds," by R. Sasin, et al., which appears in the Journal of American Chemical Society, Vol. 81, pp. 6275–6277 (1959)).

The bioactivity of these various new phosphorus containing compounds has been established in vitro but, as will be apparent to those skilled in the arts pertaining to the growth inhibition of bacteria, yeast and molds, the compounds, besides being used as such, will for utilitarian purposes commonly be formulated using a diluent that can be either liquid, gel, or solid.

A wide variety of extending agents is operable, the only significant requirement being that the diluent or extender be inert with respect to the compound involved. Petroleum jellies, various alcohols and polyols, vegetable oils and the like are suitable.

ANTIMICROBIAL EVALUATION PROCEDURE

The micro-organisms used were obtained from stock cultures. Difco Dehydrated Mycological Agar at pH 7.0 was used to test the inhibition of the test organisms by the compounds being screened. Suspensions of the test organisms were prepared by transferring a loop of spores into sterile saline. Hardened agar plates were inoculated by placing 3 drops of the suspension onto the agar. The micro-organisms were spread over the surface of the plates with sterile glass rods. These plates were employed in the activity estimation against microbial growth. Filter paper discs, 6.5 mm. in diameter made from Whatman Number 1 filter paper, were used to evaluate the compounds. The paper discs, wetted until they were completely saturated with the test compound, were placed on the surface of the agar plates inoculated with the test micro-organisms. A minimum of three experiments, at different times, employing duplicate plates were made for each compound under test. All plates were incubated at the optimum growing temperature for each micro-organism and the readings were taken after 24, 48, 72, and 120 hour periods.

The micro-organisms used in the tests were *Escherichia coli*, *Irichosporon capitatum*, *Trichodermavirde*, and *Candida lipolytica*. They were obtained from stock cultures. The various data from antimicrobial activity tests and elemental analyses are tabulated in Tables I and II, respectively.

A more detailed presentation of the material pertaining to the present invention can be found in the Journal of the American Oil Chemists Society, Vol. 49, No. 11, pp. 634-635 (1972), bearing the title "Free Radical Addition of Dialkyl Phosphites to N,N-Disubstituted Amides of Unsaturated Fatty Acids and Screening of the Products for Antimicrobial Activity."

The following examples are provided to illustrate specific embodiments of the invention. Growth inhibiting properties are presented in tabulated form. These examples are not intended to limit the invention in any manner whatever.

EXAMPLE 1

N,N-Dibutyl-9(10)-dibutylphosphonooctadecanamide. Samples of 1.5 grams (0.0038 mole) of N,N-dibutyloleamide and 2.6 grams (0.0134 mole) of dibutyl phosphite were placed in a flask, mixed well, and exposed to a cobalt-60 ($\gamma$ - radiation) source which had a dose rate of about 0.95 Mr/hr to initiate free radical chain reaction. After irradiating for 18 hours (equivalent to about 17 megarads with this source), the mixture was removed from the irradiation source, dissolved in Skelly B, passed through a column of activated alumina and stripped. The product, N,N-dibutyl-9(10)-dibutyl-phosphonooctadecanamide, had a phosphorus content of 5.01% (theory 5.27%).

EXAMPLE 2

N,N-Bis(2-ethoxyethyl)-9(10)-dibutylphosphonooctadecanamide. This compound was prepared by the procedure of Example 1 from 8 grams (.0018 mole) of N,N-bis(2-ethoxyethyl)oleamide and 11 grams (.0057 mole) of dibutylphosphite. The product, N,N-bis(2-ethoxyethyl)-9(10)-dibutylphosphonooctadecanamide had a phosphorus content of 4.75% (theory 4.99%).

EXAMPLE 3

N-[9(10)-Dibutylphosphonooctadecanoyl]-2,6-dimethylmorpholine. This compound was prepared by the procedure of Example 1 from 8 grams (.0020 mole) of N-oleoyl-2,6-dimethylmorpholine and 12.3 grams (.0063 mole) of dibutyl phosphite. The product, N-[9(10)-dibutylphosphonooctadecanoyl]-2,6-dimethylmorpholine had a phosphorus content of 5.34% (theory 5.40%).

EXAMPLE 4

N-Ethyl-N-(3-ethoxypropyl)-9(10)-dibutylphosphonooctadecanamide. This compound was prepared by the procedure of Example 1 from 8 grams (.0020 mole) of N-ethyl-N-(3-ethoxy-propyl)oleamide and 12.2 grams (.0063 mole) of dibutyl phosphite. The product, N-ethyl-N-(3ethoxypropyl)-9(10)-dibutylphosphonooctadecanamide had a phosphorus content of 5.18% (theory 5.25%).

EXAMPLE 5

N-[9(10)-Dibutylphosphonooctadecanoyl]piperidine. This compound was prepared by the procedure of Example 1 from 4 grams (.0011 mole) of N-oleoylpiperidine and 6.7 grams (.0034 mole) of dibutyl phosphite. The product, N-[9(10)-dibutylphosphonooctadecanoyl]piperidine had a phosphorus content of 5.70% (theory 5.70%).

EXAMPLE 6

N-[9(10)-Dibutylphosphonooctadecanoyl]-N'-methylpiperazine. This compound was prepared by the procedure of Example 1 from 8 grams (.0021 mole) of N-oleoyl-N'-methylpiperazine and 12.8 grams (.0066 mole) of dibutyl phosphite. The product, N-[9(10)-dibutylphosphonooctadecanoyl]-N'-methylpiperazine, had a phosphorus content of 5.32% (theory 5.55%).

EXAMPLE 7

N,N-Dimethyl-9(10)-dibutylphosphonooctadecanamide. The compound was prepared by the procedure of Example 1 from 8 grams (.0026 mole) of N,N-dimethyloleamide and 15.1 grams (.0078 mole) of dibutyl phosphite. The product, N,N-dimethyl-9(10)-dibutylphosphonooctadecanamide, had a phosphorus content of 6.28% (theory 6.15%).

EXAMPLE 8

N-[9(10)-Dibutylphosphonooctadecanoyl]-4-methylpiperidine. This compound was prepared by the procedure of Example 1 from 8 grams (.0022 mole) of N-oleoyl-4-methylpiperidine and 12.8 grams (.0066 mole) of dibutyl phosphite. The product, N-[9(10)-dibutylphosphonooctadecanoyl]-4-methylpiperidine had a phosphorus content of 5.31% (theory 5.56%).

EXAMPLE 9

N-Methyl-N-Butyl-9(10)-dibutylphosphonooctadecanamide. This compound was prepared by the procedure of Example 1 from 8 grams (.0023 mole) of N-methyl-N-butyloleamide and 13.4 grams (.0069 mole) of dibutyl phosphite. The product, N-methyl-N-butyl-9(10)-dibutylphosphonooctadecanamide, had a phosphorus content of 5.35% (theory 5.68%).

EXAMPLE 10

N-[9(10)-Dibutylphosphonooctadecancyl]morpholine. This compound was prepared by the procedure of Example 1 from 8 grams (.0023 mole) of N-oleoylmorpholine and 13.3 grams (.0068 mole) of dibutyl phosphite. The product, N-[9(10)-dibutylphosphonooctadecanoyl]morpholine, had a phosphorus content of 5.6% (theory 5.68).

EXAMPLE 11

N-[11-Dibutylphosphonoundecanoyl]morpholine. This compound was prepared by the procedure of Example 1 from 8 grams (.0032 mole) of 10-undecenoylmorpholine and 18.4 grams (.0095 mole) of dibutylphosphite. The product,-N-[11-dibutylphosphonoundecanoyl]morpholine had a phosphorus content of 6.71%(theory 6.90%).

EXAMPLE 12

N-(12-Acetyl-12-Carboethoxydodecanoyl)morpholine. Samples of 2 grams (.0078 mole) of 10-undecenoylmorpholine and 30.9 grams (0.237 mole) of ethyl acetoacetate were placed in a flask, mixed well, and exposed to a cobalt-60 (γ-radiation) source to initiate free radical chain reaction. After irradiating for 17 hours, the mixture was removed from the irradiation source and stripped under reduced pressure. Analysis of the product, N-(12-acetyl-12-carboethoxydodecanoyl) morpholine: % G 65.78 (theory 65.76); % H, 9.87 (theory 9.73); % N, 3.68 (theory 3.65).

SUMMARY OF THE INVENTION

This invention can best be described as (1) a process for the preparation of phosphonated fatty amides utilizing gamma-radiation from cobalt-60 to initiate a free-radical chain reaction to react morpholines with dialkyl phosphite to yield products represented by the formula:

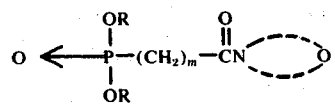

wherein R is an alkyl radical containing from one to four carbon atoms; (2) the products produced by the process of (1), which are phosphonates with substantial antimicrobial activity, such as the product N(11-dibutylphosphonoundecanoly)morpholine, which is derived from 10-undecenoyl morpholine; (3) a process for the preparation of compounds represented by either:

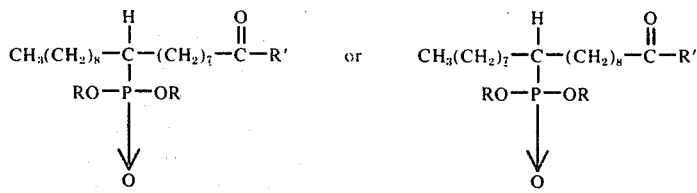

wherein R is an alkyl radical containing from one to four carbon atoms and R' contains an amide nitrogen which may be derived from a dialkylamine, alkyl-alkoxyalkylamine, or nitrogen heteroalicyclic, which process comprises reacting 1 mole of an N,N-disubstituted oleamide with about from 1 to 3 moles of a dialkyl phosphite, using gamma radiation from cobalt-60 to initiate free-radical reaction, and (4) the many phosphonated fatty amides produced by the process of (3).

N-[9(10)-Dibutylphosphonooctadecanoyl]-N'-methylpiperazine,
N-[9(10)-Dibutylphosphonooctadecanoyl]morpholine, and
N-[11-Dibutylphosphonoundecanoyl]morpholine.

2. The process of claim 1 wherein the phosphonated N,N-disubstituted fatty amide is N-[9(10)-Dibutylphosphonooctadecanoyl]-2,6-dimethylmorpholine.

3. The process of claim 1 wherein the phosphonated N,N-disubstituted fatty amide is N-[9(10)-Dibutyl-

TABLE 1

Antimicrobial Activity of Phosphonated Fatty Amides

| Compound | Antimicrobial Activity[a] Micro-organism[b] | | | |
|---|---|---|---|---|
| | A | B | C | D |
| N,N-Dibutyl-9(10)-dibutylphosphonooctadecanamide | xx | — | — | — |
| N,N-Bis(2-ethoxyethyl)-9(10)-dibutylphosphonooctadecanamide | xx | x | xx | x |
| N-[9(10)-Dibutylphosphonooctadecanoyl]-2,6-dimethylmorpholine | + | x | x | x |
| N-Ethyl-N-(3-ethoxypropyl)-9(10)-dibutylphosphonooctadecanamide | x | x | x | x |
| N[9(10)-Dibutylphosphonooctadecanoyl]piperidine | + | x | x | xx |
| N-[9(10)-Dibutylphosphonooctadecanoyl]-N'-methylpiperazine | xx | xx | x | xx |
| N,N-Dimethyl-9(10)-dibutylphosphonooctadecanamide | x | xx | xx | x |
| N-[9(10)-Dimethylphosphonooctadecanoyl]-4-methylpiperidine | xx | xx | x | x |
| N-Methyl-N-butyl-9(10)-dibutylphosphonooctadecanamide | xx | xx | xx | x |
| N-[9(10)-Dibutylphosphonooctadecanoyl]morpholine | x | x | x | x |
| N-[11-Dibutylphosphonoundecanoyl]morpholine | ++ | ++ | ++ | ++ |
| N-(12-Acetyl-12-carboethoxydodecanoyl)morpholine | x | ++ | ++ | + |

[a] ++ = The zone of inhibition was at least 0.5 cm beyond disc at 120 hrs. + = The zone of inhibition was less than 0.5 cm beyond disc at 120 hrs. xx = Organism failed to grow on disc at 120 hrs. x = Slight growth on the saturated disc at 120 hrs. — = No inhibition detectable.
[b] A = Escherichia coli; B = Trichosporon cutaneum; C = Trichoderma viride; D = Candida lipolytica.

TABLE 11

Elemental Analyses and Properties of Phosphonated Fatty Amides

| | Density 30 C | $N_D^{30}$ | % C Exp. | % C Theory | % H Exp. | % H Theory | % N Exp. | % N Theory | % P Exp. | % P Theory |
|---|---|---|---|---|---|---|---|---|---|---|
| N,N-Dibutyl-9(10)-dibutylphosphonooctadecanamide | 0.9223 | 1.4534 | 68.94 | 69.46 | 12.06 | 12.35 | 2.46 | 2.38 | 5.01 | 5.27 |
| N,N-Bis(2-ethoxyethyl)-9(10)-dibutylphosphonooctadecanamide | 0.9501 | 1.4538 | 66.28 | 65.78 | 11.23 | 11.37 | 2.27 | 2.26 | 4.75 | 4.99 |
| N-[9(10)-Dibutylphosphonooctadecanoyl]-2,6-dimethylmorpholine | 0.9661 | 1.4618 | 66.90 | 66.98 | 11.43 | 11.59 | 2.34 | 2.44 | 5.34 | 5.40 |
| N-Ethyl-N-(3-ethoxypropyl)-9(10)-dibutylphosphonooctadecanamide | 0.9411 | 1.4541 | 67.27 | 67.20 | 11.18 | 11.02 | 2.38 | 2.38 | 5.18 | 5.26 |
| N-[9(10)-Dibutylphosphonooctadecanoyl]piperidine | 0.9385 | 1.4667 | 68.05 | 68.47 | 11.54 | 11.86 | 2.65 | 2.58 | 5.70 | 5.70 |
| N-[9(10)-Dibutylphosphonooctadecanoyl]-n'methylpiperazine | 0.9514 | 1.4605 | 67.02 | 66.83 | 11.32 | 11.36 | 4.85 | 5.01 | 5.32 | 5.55 |
| N,N-Dimethyl-9(10)-dibutylphosphonooctadecanamide | 0.9495 | 1.4559 | 66.53 | 66.76 | 11.44 | 12.01 | 2.68 | 2.78 | 6.28 | 6.15 |
| N-[9(10)-Dibutylphosphonooctadecanoyl]-4-methylpiperidine | 0.9482 | 1.4643 | 69.30 | 68.90 | 11.52 | 11.93 | 2.41 | 2.51 | 5.31 | 5.56 |
| N-Methyl-N-butyl-9(10)-dibutylphosphonooctadecanamide | 0.9150 | 1.4557 | 68.06 | 68.21 | 12.11 | 11.82 | 2.74 | 2.57 | 5.35 | 5.68 |
| N-[9(10)-Dibutylphosphonooctadecanoyl]morpholine | 0.9740 | 1.4611 | 65.96 | 66.00 | 11.10 | 11.08 | 2.59 | 2.57 | 5.60 | 5.68 |
| N-[11-Dibutylphosphonoundecanoyl]morpholine | 1.0233 | 1.4728 | 61.17 | 61.71 | 10.73 | 10.36 | 3.23 | 3.13 | 6.71 | 6.90 |
| N-(12-Acetyl-12-carboethoxydodecanoyl)morpholine | — | — | 65.68 | 65.78 | 9.92 | 9.87 | 3.56 | 3.68 | — | — |

We claim:

1. A process for inhibiting fungal growth, comprising contacting said fungus with an effective fungal growth inhibitory amount of a phosphonated N,N-disubstituted fatty amide selected from the group consisting of:

N-[9(10)-Dibutylphosphonooctadecanoyl]-2,6-dimethylmorpholine, phosphonooctadecanoyl]-N'-methylpiperazine.

4. The process of claim 1 wherein the phosphonated N,N-disubstituted fatty amide is N-[9(10)-dibutylphosphonooctadecanoyl]morpholine.

5. The process of claim 1 wherein the phosphonated N,N-disubstituted fatty amide is N-[11-dibutylphosphonoundecanoyl]morpholine.

* * * * *